United States Patent [19]

Buonagurio et al.

[11] Patent Number: 5,837,818
[45] Date of Patent: *Nov. 17, 1998

[54] CONSTRUCTION AND EXPRESSION OF SYNTHETIC GENES ENCODING ENVELOPE EPITOPES OF THE HUMAN T CELL LEUKEMIA VIRUS TYPE I

[75] Inventors: Deborah A. Buonagurio, Mamaroneck, N.Y.; Mathew Longiaru, West Orange, N.J.

[73] Assignee: Roche Diagnostic Systems, Inc., Branchburg, N.J.

[ * ] Notice: The term of this patent shall not extend beyond the expiration date of Pat. No. 5,693,755.

[21] Appl. No.: 691,989

[22] Filed: Aug. 2, 1996

Related U.S. Application Data

[62] Division of Ser. No. 327,129, Oct. 21, 1994, Pat. No. 5,693,755, which is a continuation of Ser. No. 997,153, Dec. 22, 1992, abandoned, which is a continuation of Ser. No. 876,822, Apr. 29, 1992, abandoned, which is a continuation of Ser. No. 425,252, Oct. 23, 1989, abandoned.

[51] Int. Cl.$^6$ ............................ C07K 14/16; C12P 21/02; C12N 7/00; A61K 39/21
[52] U.S. Cl. ..................... 530/350; 435/69.3; 435/235.1; 435/5; 435/69.1; 424/207.1; 424/187.1; 424/184.1
[58] Field of Search .............................. 435/5, 69.3, 69.1, 435/235.1; 424/207.1, 184.1, 187.1; 530/350

[56] References Cited

U.S. PATENT DOCUMENTS 4,724,258 2/1988 Yoshida .
4,833,071 5/1989 Wang et al. .
4,939,094 7/1990 Kuga et al. .
5,003,043 3/1991 Akita et al. .

FOREIGN PATENT DOCUMENTS 0 181 107 10/1985 European Pat. Off. .
WO 90/15075 12/1990 WIPO .

OTHER PUBLICATIONS

Seiki et al. PNAS, 80:3618–3622 (1983).
Yoshida et al., PNAS, 79:2031–2035 (1982).
Parker et al., J. Immunol., 142:971–978 (1989).
Copeland et al., J. Immunol., 137:2945–2951 (Nov. 1, 1986).
Samuel et al., Science, 226:1094–1097 (Nov. 30, 1984).
Copeland et al., Biochem. and Biophys. Res. Comm., 126:672–677 (Jan. 31, 1985).

*Primary Examiner*—Jeffrey Stucker
*Assistant Examiner*—Phuong T. Bui
*Attorney, Agent, or Firm*—George W. Johnston; Dennis P. Tramaloni

[57] ABSTRACT

A synthetic gene which codes for at least one epitope from the immunodominant conserved region of HTLV-I env. gp 21 as well as hybrid genes utilizing the synthetic gene in conjunction with other epitopes from HTLV-Ienv. gp 46 and gp 21; the corresponding gene products, recombinant vectors containing the genes, methods for producing the polypeptides and methods for detecting antibodies to HTLV-I using the polypeptides of the invention

7 Claims, 19 Drawing Sheets

106aa

| ATG | AGA | GGA | TCC | GGT | AAA | TCT | CTG | CTT | CAC | GAA | GTA | GAC | AAA | GAT | ATC | AGC | CAG |
|---|---|---|---|---|---|---|---|---|---|---|---|---|---|---|---|---|---|
| MET | Arg | Gly | Ser | Gly | Lys | Ser | Leu | Leu | His | Glu | Val | Asp | Lys | Asp | Ile | Ser | Gln |

| CTG | ACT | CAG | GCT | ATC | GTT | AAA | AAC | CAC | AAG | AAC | CTG | CTG | AAA | ATC | ATC | GCT | CAG | TAC |
|---|---|---|---|---|---|---|---|---|---|---|---|---|---|---|---|---|---|---|
| Leu | Thr | Gln | Ala | Ile | Val | Lys | Asn | His | Lys | Asn | Leu | Leu | Lys | Ile | Ile | Ala | Gln | Tyr |

| GCT | GCA | CAG | AAC | CGT | CGC | GGT | CTG | GAC | CTT | TTC | TGG | GAA | CAG | GGC | GGT | GGT | CTC |
|---|---|---|---|---|---|---|---|---|---|---|---|---|---|---|---|---|---|
| Ala | Ala | Gln | Asn | Arg | Arg | Gly | Leu | Asp | Leu | Phe | Trp | Glu | Gln | Gly | Gly | Gly | Leu |

| TGC | AAA | GCT | CTG | CAG | GAA | CAG | TGC | CGT | TTC | CCG | AAC | ATC | ACT | AAC | TCC | CAC | GTA |
|---|---|---|---|---|---|---|---|---|---|---|---|---|---|---|---|---|---|
| Cys | Lys | Ala | Leu | Gln | Glu | Gln | Cys | Arg | Phe | Pro | Asn | Ile | Thr | Asn | Ser | His | Val |

| CCG | ATC | CTG | CAA | GAA | CGT | CCG | CCA | CTG | GAC | CTG | GAA | AAC | CGC | GTA | CTG | ACC | GGT | TGG | GGT |
|---|---|---|---|---|---|---|---|---|---|---|---|---|---|---|---|---|---|---|---|
| Pro | Ile | Leu | Gln | Glu | Arg | Pro | Pro | Leu | Asp | Leu | Glu | Asn | Arg | Val | Leu | Thr | Gly | Trp | Gly |

| CTG | AAC | TGG | GAC | CTG | GGA | TCC | GTC | GAC | CTG | CAG | CCA | AGC | TTA | ATT | AGC | TGA |
|---|---|---|---|---|---|---|---|---|---|---|---|---|---|---|---|---|
| Leu | Asn | Trp | Asp | Leu | Gly | Ser | Val | Asp | Leu | Gln | Pro | Ser | Leu | Ile | Ser |  |

| ATG | AGA | GGA | TCC | GGT | AAA | TCT | CTG | CTT | CAC | GAA | GTA | GAC | AAA | GAT | ATC | AGC | CAG |
|---|---|---|---|---|---|---|---|---|---|---|---|---|---|---|---|---|---|
| MET | Arg | Gly | Ser | Gly | Lys | Ser | Leu | Leu | His | Glu | Val | Asp | Lys | Asp | Ile | Ser | Gln |

| CTG | ACT | CAG | AAC | GCT | ATC | AAA | GTT | CAC | CAC | AAG | AAC | CTG | CTG | AAA | ATC | GCT | CAG | TAC |
|---|---|---|---|---|---|---|---|---|---|---|---|---|---|---|---|---|---|---|
| Leu | Thr | Gln | Asn | Ala | Ile | Lys | Val | His | His | Lys | Asn | Leu | Leu | Lys | Ile | Ala | Gln | Tyr |

| GCT | GCA | CAG | AAC | CGT | CGC | GGT | CGT | CTG | GAC | CTT | TTC | TGG | GAA | CAG | GGC | GGT | CTC |
|---|---|---|---|---|---|---|---|---|---|---|---|---|---|---|---|---|---|
| Ala | Ala | Gln | Asn | Arg | Arg | Gly | Arg | Leu | Asp | Leu | Phe | Trp | Glu | Gln | Gly | Gly | Leu |

| TGC | AAA | GCT | CTG | CAG | GAA | CAG | TGC | CGT | TTC | CCG | AAC | ATC | ACT | AAC | TCC | CAC | GTA |
|---|---|---|---|---|---|---|---|---|---|---|---|---|---|---|---|---|---|
| Cys | Lys | Ala | Leu | Gln | Glu | Gln | Cys | Arg | Phe | Pro | Asn | Ile | Thr | Asn | Ser | His | Val |

| CCG | ATC | CAA | GAA | CGT | CCG | CCA | CTG | GAA | AAC | CGC | GTA | CTG | ACC | GGT | TGG | GGT |
|---|---|---|---|---|---|---|---|---|---|---|---|---|---|---|---|---|
| Pro | Ile | Gln | Glu | Arg | Pro | Pro | Leu | Glu | Asn | Arg | Val | Leu | Thr | Gly | Trp | Gly |

| CTG | AAC | TGG | GAC | CTG | GGA | TCC | GTC | GAC | GCT | CCA | GGA | TAT | GAC | CCC | ATC | TGG | TTC |
|---|---|---|---|---|---|---|---|---|---|---|---|---|---|---|---|---|---|
| Leu | Asn | Trp | Asp | Leu | Gly | Ser | Val | Asp | Ala | Pro | Gly | Tyr | Asp | Pro | Ile | Trp | Phe |

| CTT | AAT | ACC | GAA | CCC | AGC | CAA | CTC | CCT | GAG | CCC | ACC | GCC | CCT | CCT | TGG | AAA | CCC | CAC |
|---|---|---|---|---|---|---|---|---|---|---|---|---|---|---|---|---|---|---|
| Leu | Asn | Thr | Glu | Pro | Ser | Gln | Leu | Pro | Glu | Pro | Thr | Ala | Pro | Pro | Trp | Lys | Pro | His |

| TCT | AAC | CTA | GAC | CAC | ATC | CTC | CTG | GAG | CCC | TCT | ATA | CCA | TGG | AAA | TCA | AAA | CTC | TTG |
|---|---|---|---|---|---|---|---|---|---|---|---|---|---|---|---|---|---|---|
| Ser | Asn | Leu | Asp | His | Ile | Leu | Leu | Glu | Pro | Ser | Ile | Pro | Trp | Lys | Ser | Lys | Leu | Leu |

| ACC | CTT | GTC | CAG | TTG | GAC | CGG | TCG | ACC | TGC | AGC | CAA | GCT | TAA |
|---|---|---|---|---|---|---|---|---|---|---|---|---|---|
| Thr | Leu | Val | Gln | Leu | Asp | Arg | Ser | Thr | Cys | Ser | Gln | Ala | |

```
ATG AGA GGA TCC GGT AAA TCT CTG CTT CAC GAA GTA GAC AAA GAT ATC AGC CAG
MET Arg Gly Ser Gly Lys Ser Leu Leu His Glu Val Asp Lys Asp Ile Ser Gln

CTG ACT CAG GCT ATC GTT AAA AAC CAC AAG AAC CTG CTG AAA ATC GCT CAG TAC
Leu Thr Gln Ala Ile Val Lys Asn His Lys Asn Leu Leu Lys Ile Ala Gln Tyr

GCT GCA CAG AAC CGT CGC GGT CTG GAC CTG CTT TTC TGG GAA CAG GGC GGT CTC
Ala Ala Gln Asn Arg Arg Gly Leu Asp Leu Leu Phe Trp Glu Gln Gly Gly Leu

TGC AAA GCT CTG CAA GAA CAG TGC CGT TTC CCG AAC ATC ACT AAC TCC CAC GTA
Cys Lys Ala Leu Gln Glu Gln Cys Arg Phe Pro Asn Ile Thr Asn Ser His Val

CCG ATC CTG CCA GAA CGT CCG CCA CTG GAA AAC CGC GTA CTG ACC GGT TGG GGT
Pro Ile Leu Pro Glu Arg Pro Pro Leu Glu Asn Arg Val Leu Thr Gly Trp Gly

CTG AAC TGG GAC CTG GGA TCC GTC GAC CTG CAG CCA AGC TTG GGA TCC CGC TCC
Leu Asn Trp Asp Leu Gly Ser Val Asp Leu Gln Pro Ser Leu Gly Ser Arg Ser
```

```
CGC CGA GCG GTA CCG GTG GCG GTC TGG CTT GTC TCC GCC CTG GCC ATG GGA GCC
Arg Ala Val Pro Val Ala Val Trp Leu Val Ser Ala Leu Ala MET Gly Ala

GGA GTG GCT GGC GGG ATT ACC GGC TCC ATG TCC GCC CTC GCC AAG AGC CTC
Gly Val Ala Gly Gly Ile Thr Gly Ser MET Ser Ala Leu Ala Lys Ser Leu

CTA CAT GAG GTG GAC AAA GAT ATT TCC CAA TTA ACT CAA GCA GTC AAA AAC
Leu His Glu Val Asp Lys Asp Ile Ser Gln Leu Thr Gln Ala Val Lys Asn

CAC AAT CTA CTC AAA ATT ATT GCG CAG TAT GCT ACT CAA AAC AGA CAG CTT
His Asn Leu Leu Lys Ile Ile Ala Gln Tyr Ala Thr Gln Asn Arg Gln Leu

GAT CTC CTG TTC TGG GAG CAA GGA GGA TTA TGC GCC TTA CTA CAA GAA TGC
Asp Leu Leu Phe Trp Glu Gln Gly Gly Leu Cys Ala Leu Leu Gln Glu Cys

TGT TTT CTG AAT ATT ACT CAT GTC TCT AAT ATA CTA CAA ATA GAA AGA CCC
Cys Phe Leu Asn Ile Thr His Val Ser Asn Ile Leu Gln Ile Glu Arg Pro

CTT GAA AAT CGA GTC CTG ACT GGC TGG GGC GAC TGG AAC CTT GGC CTT TCA
Leu Glu Asn Arg Val Leu Thr Gly Trp Gly Asp Trp Asn Leu Gly Leu Ser

CAG TGG GCT CGA CCT GCA GCC AAG CTC CAA GCT TAA
Gln Trp Ala Arg Pro Ala Ala Lys Leu Gln Ala
```

344aa

| ATG | AGA | GGA | TCC | GGT | AAA | TCT | CTG | CTT | CAC | GAA | GTA | GAC | AAA | GAT | ATC | AGC | CAG |
|---|---|---|---|---|---|---|---|---|---|---|---|---|---|---|---|---|---|
| MET | Arg | Gly | Ser | Gly | Lys | Ser | Leu | Leu | His | Glu | Val | Asp | Lys | Asp | Ile | Ser | Gln |

| CTG | ACT | CAG | GCT | ATC | GTT | AAA | AAC | CAC | AAG | AAC | CTG | CTG | AAA | ATC | GCT | CAG | TAC |
|---|---|---|---|---|---|---|---|---|---|---|---|---|---|---|---|---|---|
| Leu | Thr | Gln | Ala | Ile | Val | Lys | Asn | His | Lys | Asn | Leu | Leu | Lys | Ile | Ala | Gln | Tyr |

| GCT | GCA | CAG | AAC | CGT | CGC | GGT | CTG | GAC | CTT | CTT | TTC | TGG | GAA | CAG | GGC | GGT | CTC |
|---|---|---|---|---|---|---|---|---|---|---|---|---|---|---|---|---|---|
| Ala | Ala | Gln | Asn | Arg | Arg | Gly | Leu | Asp | Leu | Leu | Phe | Trp | Glu | Gln | Gly | Gly | Leu |

| TGC | AAA | GCT | CTG | CAG | GAA | CAG | TGC | CGT | TTC | CCG | AAC | ATC | ACT | AAC | TCC | CAC | GTA |
|---|---|---|---|---|---|---|---|---|---|---|---|---|---|---|---|---|---|
| Cys | Lys | Ala | Leu | Gln | Glu | Gln | Cys | Arg | Phe | Pro | Asn | Ile | Thr | Asn | Ser | His | Val |

| CCG | ATC | CTG | CAA | GAA | CGT | CCG | CCA | CTG | GAG | AAC | CGC | GTA | CTG | ACC | GGT | TGG | GGT |
|---|---|---|---|---|---|---|---|---|---|---|---|---|---|---|---|---|---|
| Pro | Ile | Leu | Gln | Glu | Arg | Pro | Pro | Leu | Glu | Asn | Arg | Val | Leu | Thr | Gly | Trp | Gly |

| CTG | AAC | TGG | GAC | CTG | GGA | TCC | GTC | GAG | CCC | TCT | ATA | CCA | TGG | AAA | TCA | AAA | CTC |
|---|---|---|---|---|---|---|---|---|---|---|---|---|---|---|---|---|---|
| Leu | Asn | Trp | Asp | Leu | Gly | Ser | Val | Glu | Pro | Ser | Ile | Pro | Trp | Lys | Ser | Lys | Leu |

| TTG | ACC | CTT | GTC | CAG | TTA | ACC | CTA | CAA | AGC | ACT | AAT | TAT | ACT | TGC | ATT | GTC | TGT |
|---|---|---|---|---|---|---|---|---|---|---|---|---|---|---|---|---|---|
| Leu | Thr | Leu | Val | Gln | Leu | Thr | Leu | Gln | Ser | Thr | Asn | Tyr | Thr | Cys | Ile | Val | Cys |

| ATC | GAT | CGT | TCT | TCT | CAG | AGC | GCC | CTA | TCC | ACT | TGG | CAC | GTC | CTT | TAC | CCC | AAC | GTC | TCT |
|---|---|---|---|---|---|---|---|---|---|---|---|---|---|---|---|---|---|---|---|
| Ile | Asp | Arg | Ser | Ser | Gln | Ser | Ala | Leu | Ser | Thr | Trp | His | Val | Leu | Tyr | Pro | Asn | Val | Ser |

| GTT | CCA | TCC | TCT | TCT | AGC | TCC | ACC | CTC | TAC | CCA | TTA | GCG | CTT | CCA | GCC |
|---|---|---|---|---|---|---|---|---|---|---|---|---|---|---|---|
| Val | Pro | Ser | Ser | Ser | Ser | Ser | Thr | Leu | Tyr | Pro | Leu | Ala | Leu | Pro | Ala |

| CCC | CAC | CTG | ACG | TTA | CCA | TTT | AAC | TGG | ACC | TGC | TTT | GAC | CCC | CAG | ATT | CAA |
|---|---|---|---|---|---|---|---|---|---|---|---|---|---|---|---|---|
| Pro | His | Leu | Thr | Leu | Pro | Phe | Asn | Trp | Thr | Cys | Phe | Asp | Pro | Gln | Ile | Gln |

*FIG. 10A*

| GCT | ATA | GTC | TCC | CCC | TGT | CAT | AAC | TCC | CTC | ATC | CTG | CCC | TTT | TCC | TTG |
|---|---|---|---|---|---|---|---|---|---|---|---|---|---|---|---|
| Ala | Ile | Val | Ser | Pro | Cys | His | Asn | Ser | Leu | Ile | Leu | Pro | Phe | Ser | Leu |

| TCA | CCT | GTT | CCC | ACC | CTA | GGA | TCC | CGC | CGA | CGA | GCG | GTA | GTG | GCG | GTC |
|---|---|---|---|---|---|---|---|---|---|---|---|---|---|---|---|
| Ser | Pro | Val | Pro | Thr | Leu | Gly | Ser | Arg | Arg | Arg | Ala | Val | Val | Ala | Val |

| TGG | CTT | GTC | TCC | CTG | GCC | ATG | GGA | GCC | GGA | GTG | GCT | GGC | ATT | ACC | GGC |
|---|---|---|---|---|---|---|---|---|---|---|---|---|---|---|---|
| Trp | Leu | Val | Ser | Leu | Ala | MET | Gly | Ala | Gly | Val | Ala | Gly | Ile | Thr | Gly |

| TCC | ATG | TCC | CTC | GCC | TCA | GGA | AAG | AGC | CTC | CAT | GAG | GTG | GAC | AAA | GAT | ATT |
|---|---|---|---|---|---|---|---|---|---|---|---|---|---|---|---|---|
| Ser | MET | Ser | Leu | Ala | Ser | Gly | Lys | Ser | Leu | His | Glu | Val | Asp | Lys | Asp | Ile |

| TCC | CAG | TTA | ACT | CAA | GCA | ATA | GTC | AAA | AAC | CAC | GAG | AAA | CTA | AAA | ATT | GCG |
|---|---|---|---|---|---|---|---|---|---|---|---|---|---|---|---|---|
| Ser | Gln | Leu | Thr | Gln | Ala | Ile | Val | Lys | Asn | His | Glu | Lys | Leu | Lys | Ile | Ala |

| CAG | TAT | GCT | GCC | AAC | AGA | CGA | CAG | CTT | GAT | TGT | CTC | CTC | CTC | CTC | GGA |
|---|---|---|---|---|---|---|---|---|---|---|---|---|---|---|---|
| Gln | Tyr | Ala | Ala | Asn | Arg | Arg | Gln | Leu | Asp | Cys | Leu | Leu | Leu | Leu | Gly |



| CAG | TAT | GCT | GCC | AAC | AGA | CGA | CAG | CTT | GAT | TGT | CTC | CTC | TTC | TGG | GAG | CAA | GGA |
|---|---|---|---|---|---|---|---|---|---|---|---|---|---|---|---|---|---|
| Gln | Tyr | Ala | Ala | Asn | Arg | Arg | Gln | Leu | Asp | Cys | Leu | Leu | Phe | Trp | Glu | Gln | Gly |

| GGA | TTA | TGC | AAA | GCA | GAA | CAA | TTA | CTG | AAT | ATT | ACT | AAT | TCC |
|---|---|---|---|---|---|---|---|---|---|---|---|---|---|
| Gly | Leu | Cys | Lys | Ala | Glu | Gln | Leu | Leu | Asn | Ile | Thr | Asn | Ser |

| CAT | GTC | TCA | ATA | CTA | CAA | GAA | AGA | CCC | CTT | GAA | AAT | CGA | GTC | CTG | ACT | GGC |
|---|---|---|---|---|---|---|---|---|---|---|---|---|---|---|---|---|
| His | Val | Ser | Ile | Leu | Gln | Glu | Arg | Pro | Leu | Glu | Asn | Arg | Val | Leu | Thr | Gly |

| TGG | GGC | CTT | AAC | TGG | GAC | CTT | GGC | CTC | TCA | CAG | TGG | GCT | CGA | CCT | GCA | GCC | AAG |
|---|---|---|---|---|---|---|---|---|---|---|---|---|---|---|---|---|---|
| Trp | Gly | Leu | Asn | Trp | Asp | Leu | Gly | Leu | Ser | Gln | Trp | Ala | Arg | Pro | Ala | Ala | Lys |

| CTT | AAT | TAG |
|---|---|---|
| Leu | Asn | |

| ATG | AGA | GGA | TCC | GGT | AAA | TCT | CTG | CTT | CAC | GAA | GTA | GAC | AAA | GAT | ATC | AGC | CAG |
|---|---|---|---|---|---|---|---|---|---|---|---|---|---|---|---|---|---|
| MET | Arg | Gly | Ser | Gly | Lys | Ser | Leu | Leu | His | Glu | Val | Asp | Lys | Asp | Ile | Ser | Gln |

| CTG | ACT | CAG | GCT | ATC | GTT | AAA | AAC | CAC | AAG | AAC | CTG | CTG | AAA | ATC | GCT | CAG | TAC |
|---|---|---|---|---|---|---|---|---|---|---|---|---|---|---|---|---|---|
| Leu | Thr | Gln | Ala | Ile | Val | Lys | Asn | His | Lys | Asn | Leu | Leu | Lys | Ile | Ala | Gln | Tyr |

| GCT | GCA | CAG | AAC | CGT | CGC | GGT | CTG | GAC | CTT | CTT | TTC | TGG | GAA | CAG | GGC | GGT | CTC |
|---|---|---|---|---|---|---|---|---|---|---|---|---|---|---|---|---|---|
| Ala | Ala | Gln | Asn | Arg | Arg | Gly | Leu | Asp | Leu | Leu | Phe | Trp | Glu | Gln | Gly | Gly | Leu |

| TGC | AAA | GCT | CTG | CAG | GAA | CAG | TGC | CGT | TTC | CCG | AAC | ATC | ACT | AAC | TCC | CAC | GTA |
|---|---|---|---|---|---|---|---|---|---|---|---|---|---|---|---|---|---|
| Cys | Lys | Ala | Leu | Gln | Glu | Gln | Cys | Arg | Phe | Pro | Asn | Ile | Thr | Asn | Ser | His | Val |

| CCG | ATC | CTG | CAA | GAA | CGT | CCG | CCA | CTG | GAA | AAC | CGC | GTA | CTG | ACC | GGT | TGG | GGT |
|---|---|---|---|---|---|---|---|---|---|---|---|---|---|---|---|---|---|
| Pro | Ile | Leu | Gln | Glu | Arg | Pro | Pro | Leu | Glu | Asn | Arg | Val | Leu | Thr | Gly | Trp | Gly |

| CTG | AAC | TGG | GAC | CTG | GGA | TCC | GTC | GAC | CTG | CAG | CCA | AGC | TTG | GGA | TCC | GTC | GAG |
|---|---|---|---|---|---|---|---|---|---|---|---|---|---|---|---|---|---|
| Leu | Asn | Trp | Asp | Leu | Gly | Ser | Val | Asp | Leu | Gln | Pro | Ser | Leu | Gly | Ser | Val | Glu |

| | | | | | | | | | | |
|---|---|---|---|---|---|---|---|---|---|---|
| CCC Pro | TCT Ser | ATA Ile | CCA Pro | TGG Trp | AAA Lys | TCA Ser | AAA Lys | CTC Leu | CTG Leu | ACC Thr | CTT Leu | GTC Val | CAG Gln | TTA Leu | ACC Thr | CTA Leu | CAA Gln |
| AGC Ser | ACT Thr | AAT Asn | TAT Tyr | ACT Thr | TGC Cys | ATT Ile | GTC Val | TGT Cys | ATC Ile | GAT Asp | CGT Arg | GCC Ala | AGC Ser | CTC Leu | TCC Ser | ACT Thr | TGG Trp |
| CAC His | GTC Val | CTA Leu | TAC Tyr | TCT Ser | CCC Pro | AAC Asn | GTC Val | TGT Cys | TCC Ser | GTT Val | CCA Pro | TCT Ser | TCT Ser | TCT Ser | ACC Thr | CCC Pro | CTC Leu |
| CTT Leu | TAC Tyr | CCA Pro | TCG Ser | TTA Leu | GCG Ala | CTT Leu | CCA Pro | TCT Ser | GTT Val | CCA Pro | TTA Leu | ACG Thr | TTA Leu | CCA Pro | AAC Asn | TGG Trp | |
| ACC Thr | CAC His | TGC Cys | TTT Phe | GAC Asp | CCC Pro | CAG Gln | ATT Ile | CAA Gln | GCT Ala | ATA Ile | GTC Val | TCC Ser | TCC Ser | CCC Pro | TGT Cys | CAT His | AAC Asn |
| TCC Ser | CTC Leu | ATC Ile | CTG Leu | CCC Pro | CCC Pro | TTT Phe | TCC Ser | TTG Leu | TCA Ser | CCT Pro | GTT Val | CCC Pro | ACC Thr | CTA Leu | GGA Gly | TCC Ser | CAA Gln |
| GCT Ala | TAA | | | | | | | | | | | | | | | | |

315aa

| ATG | AGA | GGA | TCC | GGT | AAA | TCT | CTG | CTT | CAC | GAA | GTA | GAC | AAA | GAT | ATC | AGC | CAG |
|-----|-----|-----|-----|-----|-----|-----|-----|-----|-----|-----|-----|-----|-----|-----|-----|-----|-----|
| MET | Arg | Gly | Ser | Gly | Lys | Ser | Leu | Leu | His | Glu | Val | Asp | Lys | Asp | Ile | Ser | Gln |

| CTG | ACT | CAG | GCT | ATC | GTT | AAA | AAC | CAC | AAG | AAC | CTG | CTG | GAC | AAA | ATC | GCT | CAG | TAC |
|-----|-----|-----|-----|-----|-----|-----|-----|-----|-----|-----|-----|-----|-----|-----|-----|-----|-----|-----|
| Leu | Thr | Gln | Ala | Ile | Val | Lys | Asn | His | Lys | Asn | Leu | Leu | Asp | Lys | Ile | Ala | Gln | Tyr |

| GCT | GCA | AAC | CGT | CGC | GGT | CTG | GAC | CTT | TTC | TGG | GAA | ATC | CAG | GGC | GGT | CTC |
|-----|-----|-----|-----|-----|-----|-----|-----|-----|-----|-----|-----|-----|-----|-----|-----|-----|
| Ala | Ala | Asn | Arg | Arg | Gly | Leu | Asp | Leu | Phe | Trp | Glu | Ile | Gln | Gly | Gly | Leu |

| TGC | AAA | GCT | CTG | CAA | GAA | CAG | TGC | CGT | TTC | CCG | AAC | CTG | AAC | ACT | AAC | CAC | GTA |
|-----|-----|-----|-----|-----|-----|-----|-----|-----|-----|-----|-----|-----|-----|-----|-----|-----|-----|
| Cys | Lys | Ala | Leu | Gln | Glu | Gln | Cys | Arg | Phe | Pro | Asn | Leu | Asn | Thr | Asn | His | Val |

| CCG | ATC | CTG | GAA | CGT | CCG | CCA | GAA | AAC | CGC | GTA | CTG | ACC | GGT | TGG | GGT |
|-----|-----|-----|-----|-----|-----|-----|-----|-----|-----|-----|-----|-----|-----|-----|-----|
| Pro | Ile | Leu | Glu | Arg | Pro | Pro | Glu | Asn | Arg | Val | Leu | Thr | Gly | Trp | Gly |

| CTG | AAC | TGG | GAC | CTG | GGA | TCC | GTC | GAC | CTG | CAG | CCA | AGC | TTG | GAG | CTT | GGC | ATG |
|-----|-----|-----|-----|-----|-----|-----|-----|-----|-----|-----|-----|-----|-----|-----|-----|-----|-----|
| Leu | Asn | Trp | Asp | Leu | Gly | Ser | Val | Asp | Leu | Gln | Pro | Ser | Leu | Glu | Leu | Gly | MET |

| GGT | AAG | TTT | CTC | GCC | ACT | TTG | ATT | TTA | TTC | TTC | CAG | TTC | TGC | CCC | CTC | ATC | TTC |
|-----|-----|-----|-----|-----|-----|-----|-----|-----|-----|-----|-----|-----|-----|-----|-----|-----|-----|
| Gly | Lys | Phe | Leu | Ala | Thr | Leu | Ile | Leu | Phe | Phe | Gln | Phe | Cys | Pro | Leu | Ile | Phe |

| GGT | GAT | TAC | AGC | CCC | TGC | TGT | ACT | CTC | ACA | GTT | TGT | TCG | TGG | ACC | TCC | TAC | CAC |
|-----|-----|-----|-----|-----|-----|-----|-----|-----|-----|-----|-----|-----|-----|-----|-----|-----|-----|
| Gly | Asp | Tyr | Ser | Pro | Cys | Cys | Thr | Leu | Thr | Val | Cys | Ser | Trp | Thr | Ser | Tyr | His |

| TCT | AAA | CCC | TGC | AAT | CCT | GCC | CAG | CCA | TGT | CCG | ACC | CTC | GAC | CTG | CTG |
|-----|-----|-----|-----|-----|-----|-----|-----|-----|-----|-----|-----|-----|-----|-----|-----|
| Ser | Lys | Pro | Cys | Asn | Pro | Ala | Gln | Pro | Cys | Pro | Thr | Leu | Asp | Leu | Leu |

| GCC | CTT | TCA | GCA | GAT | CAG | CTA | CAG | CCC | CCC | TGC | CCT | AAC | CTA | GTA | AGT | TAC | TYR |
|-----|-----|-----|-----|-----|-----|-----|-----|-----|-----|-----|-----|-----|-----|-----|-----|-----|-----|
| Ala | Leu | Ser | Ala | Asp | Gln | Leu | Gln | Pro | Pro | Cys | Pro | Asn | Leu | Val | Ser | Tyr | Tyr |

FIG. 12A

```
TCC AGC TAC CAT GCC ACC TAT TCC CTA TAT CTA TTC CCT CAT TGG ACT AAG AAG
Ser Ser Tyr His Ala Thr Tyr Ser Leu Tyr Leu Phe Pro His Trp Thr Lys Lys

CCA AAC CGA AAT GGC GGA GGT TAT TAT TCA GCC TCT TAT TCA GAC CCT TGT TCC
Pro Asn Arg Asn Gly Gly Gly Tyr Tyr Ser Ala Ser Tyr Ser Asp Pro Cys Ser

TTA AAG TGC CCA TAC CTG GGG TGC CAA TCA TGG ACC TGC CCC TAT ACA GGA GCC
Leu Lys Cys Pro Tyr Leu Gly Cys Gln Ser Trp Thr Cys Pro Tyr Thr Gly Ala

GTC TCC AGC CCC TAC TGG AAG TTT CAA CAC GAT GTC AAT TTT ACT CAA GAA GTT
Val Ser Ser Pro Tyr Trp Lys Phe Gln His Asp Val Asn Phe Thr Gln Glu Val

TCA CGC CTC AAT ATT AAT CTC CAT TTT TCA AAA TGC GGT TTT CCC TTC TCC CTT
Ser Arg Leu Asn Ile Asn Leu His Phe Ser Lys Cys Gly Phe Pro Phe Ser Leu

CTA GTC GAC GCT CCA GGA TAT GAC CCC ATC TGG TTC AAT ACC GAA CCC AGC
Leu Val Asp Ala Pro Gly Tyr Asp Pro Ile Trp Phe Leu Asn Thr Glu Pro Ser

CAA CTG CCT CCC ACC GCC CCT CTA CTC CCC CAC TCT AAC CTA GAC CAC ATC
Gln Leu Pro Pro Thr Ala Pro Leu Leu Pro His Ser Asn Leu Asp His Ile

CTC GAC CAA GCT CCA AGC TTA ATT AGC TGA
Leu Asp Gln Ala Pro Ser Leu Ile Ser
```

```
ATG AGA GGA TCC GGT AAA TCT CTG CTT CAC GAA GTA GAC AAA GAT ATC AGC CAG
MET Arg Gly Ser Gly Lys Ser Leu Leu His Glu Val Asp Lys Asp Ile Ser Gln

CTG ACT CAG GCT GTT ATC AAA AAC CAC AAG AAC CTG CTG AAA CTG CTG ATC GCT CAG TAC
Leu Thr Gln Ala Val Ile Lys Asn His Lys Asn Leu Leu Lys Leu Leu Ile Ala Gln Tyr

GCT GCA AAC CGT CGC GGT CGC GAC CTG GAA CAG GGC GGT GGT CTC
Ala Ala Asn Arg Arg Gly Arg Asp Leu Glu Gln Gly Gly Gly Leu

TGC AAA GCT CTG CAG GAA CAG TGC CGT TTC TTC CCG AAC ATC TCC CAC GTA
Cys Lys Ala Leu Gln Glu Gln Cys Arg Phe Phe Pro Asn Ile Ser His Val

CCG ATC CAA GAA CGT CCA CTG GAA CTG GAA CGC GTA CTG ACC GGT TGG GGT
Pro Ile Gln Glu Arg Pro Leu Glu Leu Glu Arg Val Leu Thr Gly Trp Gly

CTG AAC TGG GAC CTG GGA TCC GTC GAC CGC TGC TGT ACT CTC ACA ATT GGA GTC
Leu Asn Trp Asp Leu Gly Ser Val Asp Arg Cys Cys Thr Leu Thr Ile Gly Val

TCC TCA TAC CAC TCT AAA CCC TGC AAT CCT GCC CAG CCA GTT TGT TCG TGG ACC
Ser Ser Tyr His Ser Lys Pro Cys Asn Pro Ala Gln Pro Val Cys Ser Trp Thr

CTC GAC CTG CTG GCC CTT TCA GCA GAT CAG GCC CTA CAG CCC CCC TGC CCT AAC
Leu Asp Leu Leu Ala Leu Ser Ala Asp Gln Ala Leu Gln Pro Pro Cys Pro Asn

CTA GTA TAC TCC AGC CAT TAC TCC ACC GCC TAT CTA TAT CTA TTC CCT CAT
Leu Val Tyr Ser Tyr Ser His Ala Thr Ala Tyr Leu Tyr Leu Phe Pro His
```

```
TGG ACT AAG AAG CCA AAC CGA AAT GGC GGA GGC TAT TAT TCA GCC TCT TAT TCA
Trp Thr Lys Lys Pro Asn Arg Asn Gly Gly Gly Tyr Tyr Ser Ala Ser Tyr Ser

GAC CCT TGT TCC TTA AAG TGC CCA TAC CTG GGG TGC CAA TCA TGG ACC TGC CCC
Asp Pro Cys Ser Leu Lys Cys Pro Tyr Leu Gly Cys Gln Ser Trp Thr Cys Pro

TAT ACA GGA GCC GTC TCC AGC CCC TAC TGG AAG TTT CAA CAC GAT GTC AAT TTT
Tyr Thr Gly Ala Val Ser Ser Pro Tyr Trp Lys Phe Gln His Asp Val Asn Phe

ACT CAA GAA GTT TCA CGC CTC AAT ATT AAT CTC CAT TTT TCA AAA TGC GGT
Thr Gln Glu Val Ser Arg Leu Asn Ile Asn Leu His Phe Ser Lys Cys Gly

CCC TTC TCC CTT CTA GTC GAC GGT CGA CCT GCA GCC AAG CTT AAT TAG
Pro Phe Ser Leu Leu Val Asp Gly Arg Pro Ala Ala Lys Leu Asn
```

| ANTIGEN: SAMPLE | Env 93-HTLVI-I x̄ O.D. | Env 93-HTLVI-II x̄ O.D. | Env 93-HTLVI-II-I x̄ O.D. |
|---|---|---|---|
| HTLVI POS. SAMPLE | | | |
| BBI 6595 | 1.697 | 2.100 | 2.200 |
| BBI 9100 | 1.583 | 1.041 | 2.199 |
| BBI 0206-1 | 1.086 | .259 | 1.243 |
| BBI 0505-2 | .848 | .210 | 1.129 |
| BBI 0707-1 | .612 | .255 | 1.056 |
| BBI 0708-2 | .695 | .140 | .787 |
| BBI 0707-6 | .475 | .102 | .660 |
| HTLVI NEG. SAMPLE | | | |
| WSP #1 | .046 | .048 | .055 |
| WSP #2 | .032 | .043 | .042 |
| WSP #5 | .059 | .066 | .054 |
| WSP #7 | .032 | .042 | .089 |
| WSP #8 | .031 | .038 | .060 |
| WSP #9 | .047 | .056 | .056 |

FIG. 14

CONSTRUCTION AND EXPRESSION OF SYNTHETIC GENES ENCODING ENVELOPE EPITOPES OF THE HUMAN T CELL LEUKEMIA VIRUS TYPE I

This is a division of application Ser. No. 08/327,129, filed Oct. 21, 1994, now U.S. Pat. No. 5,693,755 which is a continuation of Ser. No. 07/997,153, filed Dec. 22, 1992 (abandoned); which is a continuation of Ser. No. 07/876,822, filed Apr. 29, 1992 (abandoned); which is a continuation of Ser. No. 07/425,252, filed Oct. 23, 1989 (abandoned).

TECHNICAL FIELD

The invention is directed to a synthetic gene which codes for at least one epitope from the immundominant conserved region of the HTLV-1 gp21, envelope protein as well as hybrid genes which contain this synthetic gene in conjunction with other nucleotide sequences which code for one or more epitopes from the gp 46 and gp 21 regions of the HTLV-I envelope protein. Also included are the corresponding polypeptides, recombinant vectors containing the genes, unicellular host-organisms containing such vectors, methods for producing the polypeptides, and methods for detecting antibodies to HTLV-I using the polypeptides of the invention.

BACKGROUND OF THE INVENTION

Human T-cell leukemia virus type I (HTLV-I) is a type C retrovirus which is endemic in some areas of Japan, the Caribbean, Africa, the southeastern United States, and South America. In Japan more than 1% of the nine million blood donors were believed to be infected with the virus prior to blood screening and as many as 35% of the population of Okinawa may be infected (Swinbanks, *Nature* 323: 384 (1986). HTLV-I is the etiologic agent of adult T-cell leukemia (ATL), an aggressive leukemia attacking predominantly the T4 helper cells. ATL patients produce antibodies to the major viral proteins and the proviral DNA can be found integrated into the DNA of the leukemic cells. A number of HTLV-I proviral genomes have been molecularly cloned and the entire nucleotide sequence of one of the proviral DNAS has been determined (Seiki et al., *P.N.A.S. USA.* 80: 3618 (1983). HTLV-I is associated with a number of neurological disorders including tropical spastic paraparesis, HTLV-I associated myelopathy, and multiple sclerosis. HTLV-I may also play an indirect role in the development of B-cell chronic lymphocytic leukemia.

The modes of transmission of HTLV-I are similar to those of the human immunodeficiency virus (HIV-1), the causative agent of AIDS. Transmission of HTLV-I can occur through sexual contact, transfusion of antibody-positive blood and blood components, and by sharing of contaminated needles among drug abusers. The virus can pass from mother to child across the placenta or through passage of infected lymphocytes in breast milk. The apparent similarities between modes of transmission of HIV-1 and HTLV-I would indicate that populations at risk for HIV-1 infection would also be at risk for HTLV-I infection. There have been numerous reports of AIDS patients who possess antibodies to HTLV-I. Although the prevalence of HTLV-I infection in the general U.S. population is still quite low (less than 1%), the virus has surfaced among intravenous drug users. In addition, a high incidence of human T-cell leukemia virus type II (HTLV-II) seropositivity has been reported for this population.

HTLV-II is closely related to HTLV-I (cross-reactive antigens) and was originally isolated from a patient with hairy cell leukemia. A study by Williams and co-workers (1988) on the seroprevalence of HTLV-I infection in U.S. blood donors demonstrates that 0.025% of random blood donors in eight geographically diverse areas of the United States presented serological evidence of HTLV-I infection. Based on this prevalence of HTLV-I infection, the investigators predict the infection of approximately 2800 blood recipients annually.

The American Red Cross began screening donor blood for HTLV-I in December of 1988 to protect the nation's blood supply and halt the spread of HTLV-I infection. The antibody screening tests which have been approved by the Food and Drug Administration incorporate semi-purified disrupted virus grown in human T-cell lines as the test antigen in an immunoassay format. There are inherent problems with viral lysate assays as evidenced by HIV-1 screening tests, one of which is a high rate of false positivity.

The desirability of utilizing recombinant DNA technology to prepare HTLV-I antigens for incorporation into an HTLV-I antibody screening assay is obvious for the use of recombinant proteins as test antigens should lead to the design of immunoassays with enhanced sensitivity and specificity over the viral lysate tests currently available.

SUMMARY OF THE INVENTION

The instant invention comprises:

A nucleotide sequence coding for a polypeptide containing at least one epitope from the immunodominant conserved region of the gp 21 region of the HTLV-I envelope protein (HTLV-I env.).

A hybrid gene comprised of a first nucleotide sequence coding for a polypeptide containing at least one epitope from the immunodominant conserved region of the gp 21 region of HTLV-I env. fused to a second nucleotide sequence coding for a polypeptide containing at least one epitope from the gp 46 and gp 21 region of HTLV-I env.

the polypeptides corresponding to the nucleotide sequences of the invention recombinant vectors containing the nucleotide sequences of the invention unicellular host organisms containing recombinant vectors comprised of the nucleotide sequences of the invention a method for producing the polypeptides of the invention by utilizing the unicellular host containing the recombinant vector under appropriate conditions to produce the corresponding hybrid proteins a method for detecting antibodies to HTLV-I envelope proteins comprising using the polypeptides of the invention as antigens.

BRIEF DESCRIPTION OF DRAWINGS

FIG. 4: Illustrates the nucleotide and deduced amino acid sequence of the recombinant ENV93 protein expressed from the pDS56/RBSII vector. The translated protein is 106 amino acids in length. The underlined amino acids at the amino and carboxy termini are derived from vector sequences. The remainder of the protein is the 93 amino acids corresponding to amino acids 342–434 of the gp21 transmembrane envelope protein of the HTLV-I virus.

FIG. 8: Illustrates the nucleotide and deduced amino acid sequence of the expressed ENV93/HTLVI-IIIB' recombinant protein. The protein is 158 amino acids in length. The underlined residues are the result of either vector sequences or linker sequences used to generate the construct.

FIG. 9: Illustrates the nucleotide and deduced amino acid sequence of the ENV93/HTLVI-I fusion protein. The polypeptide is 245 amino acids. The underlined amino acid residues are not represented in the HTLV-I envelope sequence. These irrelevant sequences are either vector-specific or encoded by the synthetic linkers used to generate the DNA construct.

FIG. 10: Illustrates the nucleotide and deduced amino acid sequence of the ENV93/HTLVI-II+I recombinant envelope protein. The polypeptide is 344 amino acids in length. The underlined nonspecific residues are encoded by vector sequences.

FIG. 11: Illustrates the nucleotide and deduced amino acid sequence of the ENV93/HTLVI-II recombinant protein. The protein is 217 amino acids in length. The underlined residues are encoded by either vector sequences or synthetic linkers used to generate the construct.

FIG. 12: Illustrates the nucleotide and deduced amino acid sequence of the ENV93/HTLVI-III fusion protein. The polypeptide is 315 amino acids in length. The underlined nonspecific residues are encoded by either vector or synthetic linker sequences.

FIG. 13: Illustrates the nucleotide and deduced amino acid sequence of the ENV93/HTLVI-IIIA recombinant envelope protein. The protein is 249 amino acids in length. The underlined residues are contributed by vector or synthetic linker sequences.

FIG. 14: Illustrates the immunoreactivity of various HTLV-I recombinant proteins. $OD_{492}$ values are presented for ENV93/HTLVI-I, ENV93/HTLVI-II, and ENV93/HTLVI-II+I. The HTLV-I positive samples were obtained from Boston Biomedical, Inc. (BBI) and the negative samples were purchased from Western States Plasma Company, Inc. (WSP). Samples #6595 and #9100 represent highly reactive positive controls.

DETAILED DESCRIPTION

Figure 1:
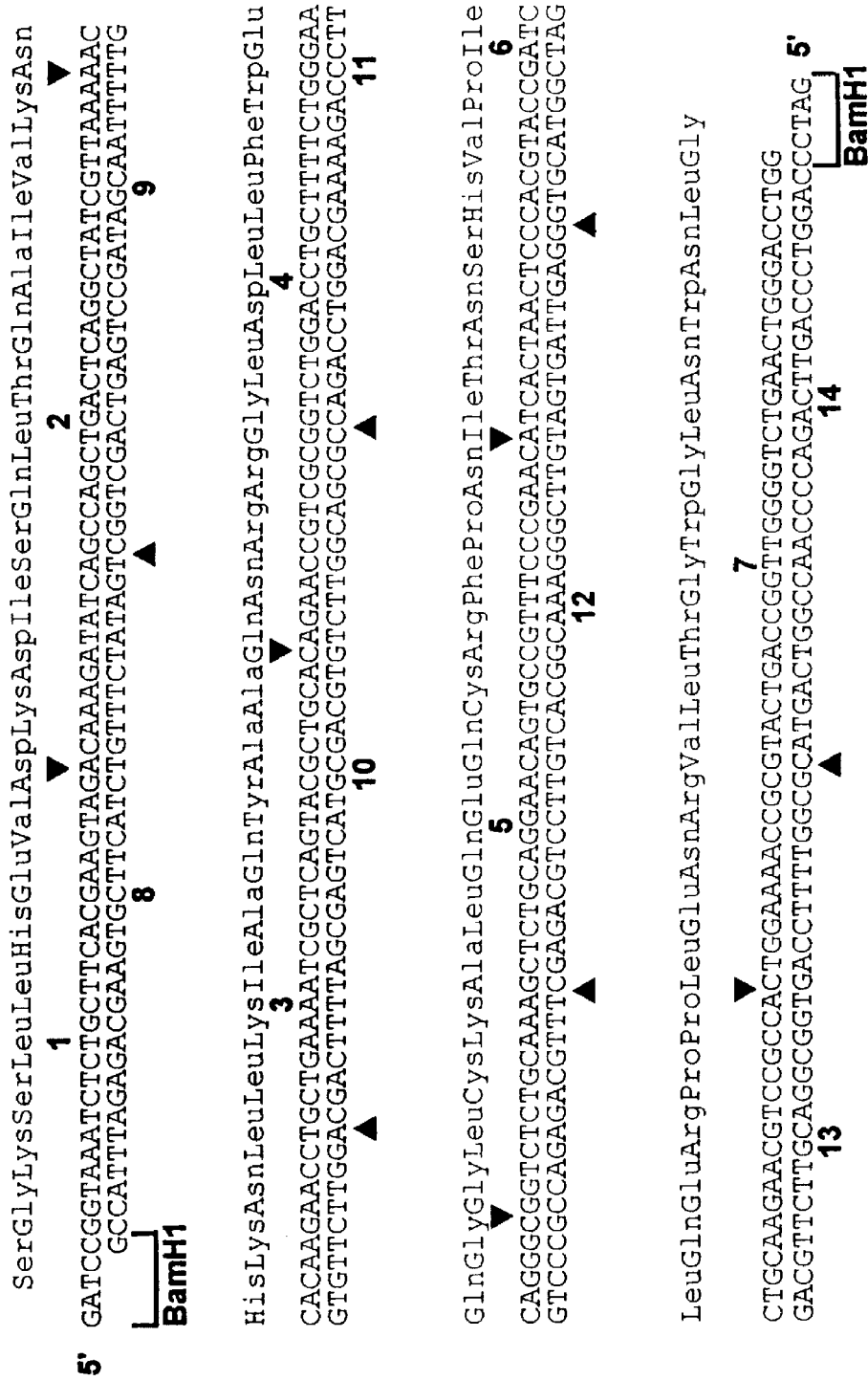
FIG. 1: Illustrates the nucleotide sequence of the ENV93 synthetic gene. The top strand represents the coding sequence. The amino acid sequence corresponds to amino acids 342–434 of the HTLV-1 envelope polyprotein within the gp21 transmembrane region. The authentic proviral DNA sequence as was transposed into codons preferentially used in *E. coli* genes which are expressed at high levels. BamHI sticky ends were incorporated into the 5' ends of the construct to facilitate insertion into the unique BamHI site of the pDS56/RBSII expression vector. The arrowheads delineate the oligonucleotides 1–14 which were annealed and ligated in four blocks to arrive at the final product.

The methods of this invention entail a number of steps which, in logical sequence, include (1) preparation of the genes encoding the gene construct of the invention, (2) insertion of these genes into an appropriate cloning vehicle to produce a recombinant vector containing the Gene constructs, (3) transfer of the recombinant cloning vehicle into a compatible host organism, (4) selection and growth of such modified hosts that can express the inserted gene sequences, (5) identification and purification of the gene product, and (6) use of the gene product to detect antibodies against HTLV-I.

1. Preparation of the genes

The first gene construct of the invention constitutes a nucleotide sequence coding for a polypeptide containing at least one epitope from the immunodominant conserved region of the gp 21 region of HTLV-I env. The entire nucleotide sequence of the HTLV-I genome has been determined (see Seiki, et al. *P.N.A.S. USA,* 80: 3618 (1983). Any portion of this sequence which codes for at least one epitope from the immunodominant conserved region will be suitable for the gene construct of the invention. It is preferred however, that the nucleotide sequence used to construct the preferred embodiment of the invention, which is designated Env(93), correspond to amino acids 342–434 of the HTLV-1 envelope (numbered according to Seiki). The nucleotide sequence may be constructed by methods well known in the art such as chemical synthesis using a DNA synthesizer (Certa, et al., *EMBO J:* 5: 3051). The appropriate nucleotide sequences may also be obtained from human T-cell lines which have been virally transformed by HTLV-1 virions as set forth in Yoshida et al., *PNAS USA* 79: 2031 (1982) and Poiesz, et al. *PNAS USA* 77: 7415 (1980). The DNA fragments can then be isolated by methods known in the art, a cDNA library constructed, and the desired envelope gene fragments obtained by probing the cDNA library. HTLV-I envelope fragments may also be obtained from plasmids such as the plasmid designated dCRX1 which contains Env, pX, and LTR of HTLV-I as described in Manzari, et al. *PNAS USA* 80: 1574 (1983) and European Patent Application publication No. 0181 107.

In the preferred embodiment of the invention a nucleotide sequence corresponding to amino acids 342–434 of the HTLV-I envelope are made by chemical synthesis methods. To facilitate synthesis the gene sequence is subdivided into oligonucleotide fragments which are constructed on a DNA synthesizer. The single stranded DNA fragments were then isolated from the gel after polyacrylamide gel electrophoresis. The nucleotide subsequences were then assembled in a stepwise ligation to yield the gene construct designated Env(93):

ENV(93)/HTLV-I(I)
as set forth in FIG. 9
ENV(93)/HTLV-I(II)
as set forth in FIG. 11
ENV(93)/HTLV-I (II+I)
as set forth in FIG. 10
ENV(93)/HTLV-I (III)
as set forth in FIG. 12
ENV(93)/HTLV-I (IIIA)
as set forth in FIG. 13
ENV(93)/HTLV-I (IIIB')
as set forth in FIG. 8

2. Preparation of the polypeptides

The instant invention also comprises the polypeptides which correspond to the gene constructs mentioned above. The polypeptides may be made by synthetic methods well known to those skilled in the art such as solid-phase or solution-phase synthesis as well as recombinant production. With recombinant methods, the gene construct is inserted into the appropriate vector of plasmid or phage origin. Convenient expression vectors of plasmid or phage origin are mentioned, for example, in the laboratory manual "Molecular Cloning" by Maniatis et al., Cold Spring Harbor Laboratory, 1982.

In the preferred embodiment of the invention the polypeptide corresponds to at least one epitope from the immunodominant conserved region of the gp21 region of HTLV-I env, preferably amino acids 342–434 of the gp21 region of HTLV-I env. having the amino acid sequence set forth in FIG. 4 (Env 93).

The ENV93 polypeptide may be used alone or as part of a hybrid polypeptide or fusion protein. When used as part of a hybrid polypeptide the first sequence corresponding to at least one epitope from the immunodominant conserved region of HTLV-I env. is fused to a second amino acid

```
ATG AGA GGA TCC GGT AAA TCT CTG CTT CAC GAA GTA GAC AAA GAT ATC AGC CAG
CTG ACT GCA GCT ATC GTT AAA AAC CAC AAG AAC CTG CTG AAA GCT CAG TAC
GCT GCA CAG AAC CGT CGC GGT CTG GAC CTG CTT TTC TGG GAA CAG GGC GGT CTC
TGC AAA GCT CTG CAG GAA CAG TGC CGT TTC CCG AAC ATC ACT AAC TCC CAC GTA
CCG ATC CTG CAA GAA CGT CCG CCA CTG GAA AAC CGC GTA CTG ACC GGT TGG GGT
CTG AAC TGG GAC CTG GGA TCC GTC GAC CTG CAG CCA AGC TTA ATT AGC TGA
```

The utility of ENV(93) gene construct is that is may be used alone or as a convenient vehicle for high level expression of other epitopes of HTLV-I env as fusion proteins. When ENV(93) is used as a vehicle it is used as part of a hybrid gene which contains Env (93) fused to a nucleotide sequence which codes for one or more epitopes from the gp 46 and gp 21 regions of the HTLV-I envelope protein. For example, in the preferred embodiment of the invention ENV(93) has been fused to various subsequences falling within the gp 46 and gp 21 regions as set forth in FIGS. 6 and 7. The instant invention is also directed to these hybrid genes which consist of ENV(93) fused to the following portions of HTLV-I env.:

nucleotides 6101–6499 (I)
nucleotides 5780–6103 (II)
nucleotides 5180–5779 (III)
nucleotides 5255–5677 (IIIA)
nucleotides 5780–6499 (II+I)
nucleotides 5672–5827 (IIIB')

The resulting hybrid genes (with the deduced amino acid sequences set forth below) are as follows:

sequence which codes for one or more epitopes from the gp46 and gp21 regions of HTLV-I env. In the preferred embodiment ENV93 is fused to various subsequences falling within the gp46 and gp21 regions as set forth below:

a) amino acids 308–440 of gp46 and gp21 (I)
b) amino acids 201–307 of gp46 (II)
c) amino acids 201–440 of gp46 and gp21 (II+I)
d) amino acids 1–200 of gp46 (III)
e) amino acids 26–165 of gp46 (IIIA)
f) amino acids 166–216 of gp46 (IIIB')

The sequences are as set forth in FIGS. 4, 8, 9, 10, 11, 12, 13.

Amino acid substitutions which do not essentially alter the biological activities of proteins are known in the art and described e.g. by H. Neurath and R. L. Hill in "The Proteins", Academic Press, New York (1979). The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/GLy, and vice versa. Any polypeptides containing such substitutions are deemed to be within the scope of the invention.

3. Preparation of the recombinant vector containing the ENV(93) construct

Figure 3:
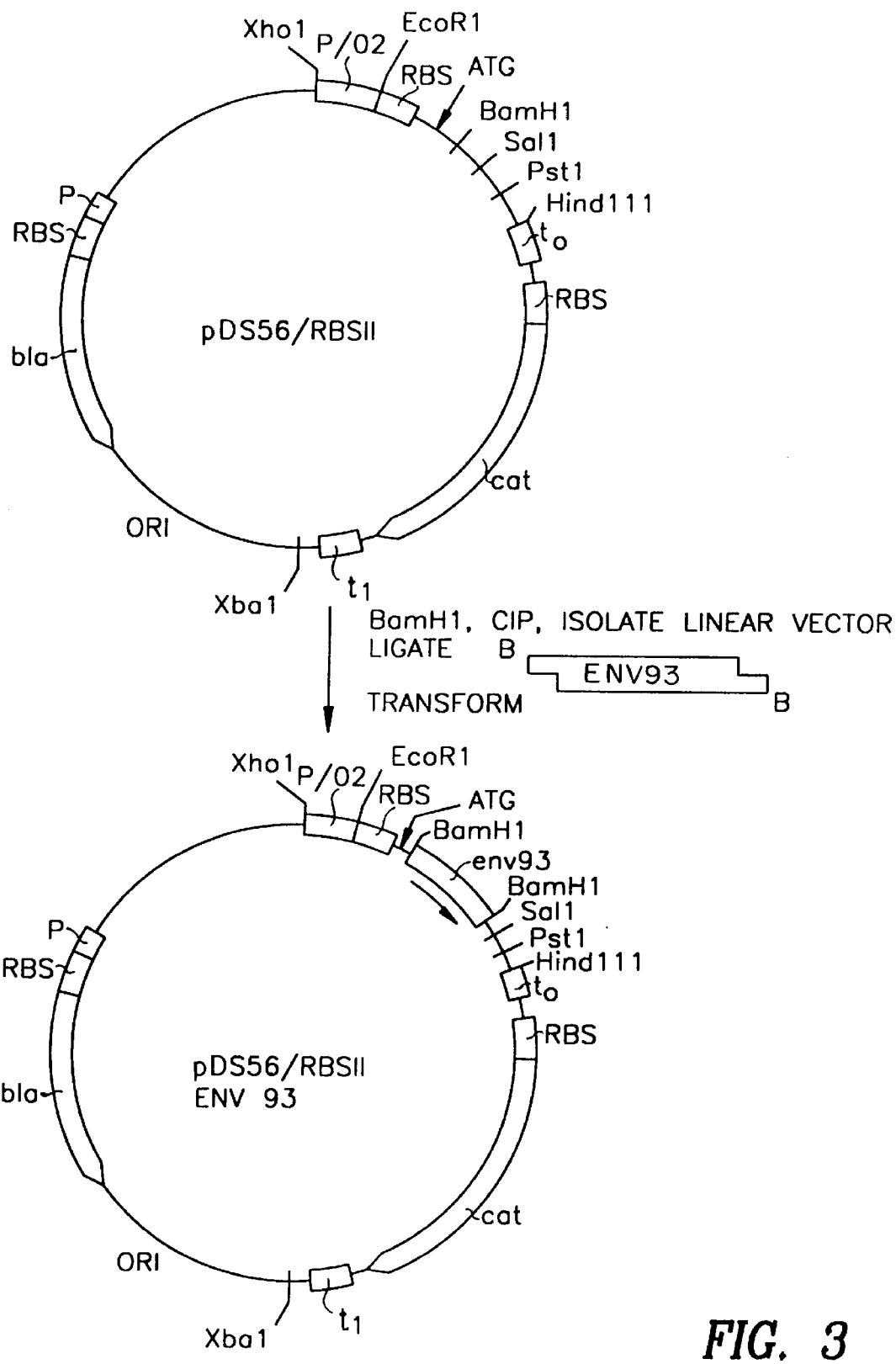
FIG. 3: Illustrates the insertion of the ENV93 construct into the BamHI site of pDS56/RBSII. Vector pDS56/RBSII (Stuber et al., *EMBO J.* 3: 3143 (1984) has been engineered for the expression of foreign genes in *E. coli*. The polylinker cloning region is flanked by the regulatable promoter/operator element P/02 (fusion between the coliphage T5 promoter and the *E. coli* lac operator) and the lambda $t_0$ terminator. Two *E. coli* indicator genes are present: bla (B-lactamase) with its own promoter and ribosome binding site conferring resistance to ampicillin and cat (chloramphenicol acetyltransferase) with its authentic ribosome binding site. The cat gene is followed downstream by the $t_1$ terminator of the rrnB operon to prevent readthrough transcription of cat into the plasmid origin of replication derived from pBR322. Immediately upstream of the polylinker site, the ATG start codon is provided along with the synthetic ribosome binding site RBSII. The pDS56/RBSII expression system is comprised of three vectors differing in the number of bases adjacent to the ATG condon which allows all three reading frames of the foreign DNA to be expressed. These vectors can only be stably maintained in *E. coli* cells harboring the compatible plasmid pDMI-1. pDMI-1 overproduces the lac repressor and confers resistance to kanamycin through expression of the neomycin phosphotransferase gene.

In the preferred embodiment of the invention the Env (93) gene construct is inserted into a vector which has been engineered for the expression of foreign genes in *E. coli* such as Vector pDS56/RBSII (Steuber, *EMBO J.*, 3: 3143 (1984). FIG. 3 and its legend illustrate this process in detail. Other vectors however, may be suitable such as *E. coli* strains containing plasmids useful for these constructions for example, *E. coli* M15 transformed with pDS8/RBSII, or *E. coli* TB1 transformed with plasmid pA-env-20. These organisms have been deposited at Deutsche Sammlung von Microorganisms (DMS) under Accession No.s DSM 3517, DSM 3519, and DSM 3516. A variety of other recombinant vectors and unicellular hosts are suitable so long as they facilitate expression of the polypeptide of the invention.

4. Method of recombinantly Producing the peptides of the Invention

The method of recombinantly producing the peptides of the invention is explained in detail in the Figures and Examples and consists generally of culturing the unicellular host containing the recombinant vector under appropriate conditions to produce the corresponding hybrid proteins.

5. A Method for detecting antibodies to HTLV-I envelope proteins

The development of an antibody screening test for HTLV-I based on recombinant viral proteins requires 1) the selection of an epitope(s) which is immunodominant and conserved among virus isolates; 2) high level expression of the epitope in an appropriate vector/host system; and 3) purification of the recombinant protein to homogeneity and in large quantity from the host in which it is produced. To achieve this goal, ENV(93) which encodes amino acids 342–434 of the HTLV-I envelope protein within the gp21 moiety was synthesized by chemical and enzymatic methods. This domain of the envelope was selected because the corresponding region (gp4l) of the HIV-1 envelope contains a number of conserved and immunoreactive epitopes (Wang et al., *P.N.A.S., USA* 83: 6159 (1986); Gnann et al., *J. Virol.*, 61: 2639 (1987) and *J. Infect. Dis.*, 156: 261 (1987). In addition, the hydropathicity profiles of both the HTLV-I and HIV-1 envelope polypeptides in the transmembrane domain exhibit similar patterns indicating that this region of the HTLV-I envelope may be important in the immune response. The authentic nucleotide sequence coding for amino acids 342–434 of the envelope protein was altered so that codons infrequently used in translation of *E. coli* proteins were replaced by those preferred by the *E. coli* translational machinery (Ikemura, *J. Mol. Bio.*, 146: 1 (1981); Grosjean and Fiers, *Gene*, 18: 199 (1982). This strategy was adopted in hopes of maximizing expression of the ENV93 epitope in the bacterial host. A similar approach was taken in the construction of an HIV-1 synthetic gene which resulted in high level expression of the encoded epitopes in *E. coli* (Certa et al., *EMBO J.*, 5: 3051 (1986).

The polypeptides of the invention may be used as diagnostic reagents for the detection of antibodies to HTLV-I according to methods well-known in the art.

For example, the "Western Blotting" analysis [Tobin, et al., *P.N.A.S. USA* 76: 4350 (1979)] would be suitable. According to this technique a polypeptide of the present invention is transferred from the SDS-polyacrylamide gel electrophoretically on to nitrocellulose paper. This nitrocellulose paper is then treated with the serum to be tested. After washing, the nitrocellulose paper is then treated with an anti-human IgG labeled with peroxidase. The peroxidase is then determined by a suitable substrate, e.g. with o-phenylenediamine. Of course other labels like radioactive or fluorescence labels may be used.

A more convenient technique for the determination of antibodies to HTLV-I using the polypeptides of the invention is an enzyme-linked immunosorbant assay (ELISA). Such assay comprises:

(a) immobilizing a polypeptide of the invention on a solid support;

(b) contacting a human serum sample suspected to contain antibodies against HTLV-I with the immobilized polypeptide of step and allowing immobilizing polypeptide-antibody complex to form;

(c) washing away unbound material from the complexes of step and;

(d) detecting such complexes by the addition of a labeled reagent capable of selectively detecting human antibodies, such as labeled *Staphylococcus aureus* protein A or anti-human IgG, thereby demonstrating the presence of antibodies against HTLV-I viruses in the serum.

Suitable solid supports are the inner wall of test vessels (test tube, titer plates, cuvettes or glass or artificial material) as well as the surface of solid bodies (rods of glass and artificial material, rods with terminal thickening, rods with terminal lobes or lamellae). Beads of glass or artificial material are especially suitable solid phase carriers.

Useful labels are any detectable functionalities which do not interfere with the binding of reagent and its binding partner. Numerous labels are known for use in ELISA assays and other immuno assays such as horseradish peroxidase, radioisotopes such as $^{14}C$ and $^{131}I$, fluorophores such as rare earth chelates or fluorescein, spin labels and the like.

In a preferred embodiment of the present invention an ELISA (EIA) assay is run utilizing the polypeptides of the invention, immobilized on beads as set forth in Example 9.

Another suitable method for the determination of antibodies against HTLV-I with the polypeptides of the invention is an enzyme immunological test according to the so-called "Double-Antigen-Sandwich-Method". This method is based on the work of Maiolini, *Immunological Methods* 20: 25-(1978). According to this method the serum to be tested is contacted with a solid support as defined above on which a polypeptide of the present invention is coated and with a polypeptide of the present invention which is labeled with peroxidase. The immunological reaction can be performed in one or in two steps. If the immunological reaction is performed in two steps then a washing step is performed between the two incubation. After the immunological reaction or reactions a washing step is performed. Thereafter the peroxidase is determined with a substrate, such as o-phenylene diamine. The present invention will be further described in connection with the following Examples which are set forth for the purposes of illustration only.

EXAMPLE 1

Synthesis of ENV93 Oligonucleotides

The synthetic gene was subdivided into 14 oligonucleotide fragments (FIGS. 1 and 2) in such a way as to achieve single-strand sequence overlaps of 12–14 nucleotides. The resulting fragments were 30–46 bases in length. The individual oligonucleotides were constructed on a MilliGen 7500 and Applied Biosystems 380 DNA synthesizer using derivatized controlled pore glass as the solid support. The single-stranded DNA fragments were isolated from a 12% polyacrylamide gel containing 7M urea and desalted over a Sep-Pak C18 cartridge (Waters Associates/Millipore). DNA concentration was determined by measuring UV absorbance at 260 nm on a spectrophotometer.

EXAMPLE 2

Assembly of ENV93 Gene

Two micrograms (150 pmoles) of oligonucleotides 2–13 were kinased in separate 50 ul reactions consisting of 50 mM Tris-HCl, pH 7.5; 10 mM $MgCl_2$, 5 mM DTT, 0.1 mM spermidine, 0.1 mM EDTA, 0.1 mM ATP, 0.21 pmoles-$^{32}$P-ATP (3,000 Ci/mmole), and 5 units of T4 polynucleotide kinase (New England Biolabs). The reactions were incubated at 37° C. for 40 minutes followed by 10 minutes at 70° C. to inactivate the kinase. The unincorporated radioactivity in each reaction was removed by G-50 Sephadex spun column chromatography. The 5' terminal fragments, oligonucleotides 1 and 14, were not phosphorylated to prevent the formation of polymers during the subsequent annealing and ligation reactions. Phosphorylated oligonucleotides 2–13 were dried down under vacuum and resuspended in 20 ul of ligation buffer without DTT and ATP (50 mM Tris-HCl, pH 7.5; 10 mM $MgCl_2$). Ten ul (1 ug) was taken for the actual gene construction. One ug of end fragments I and 14 was lyophilized and resuspended in 10 ul of the same ligation buffer.

Figure 2:
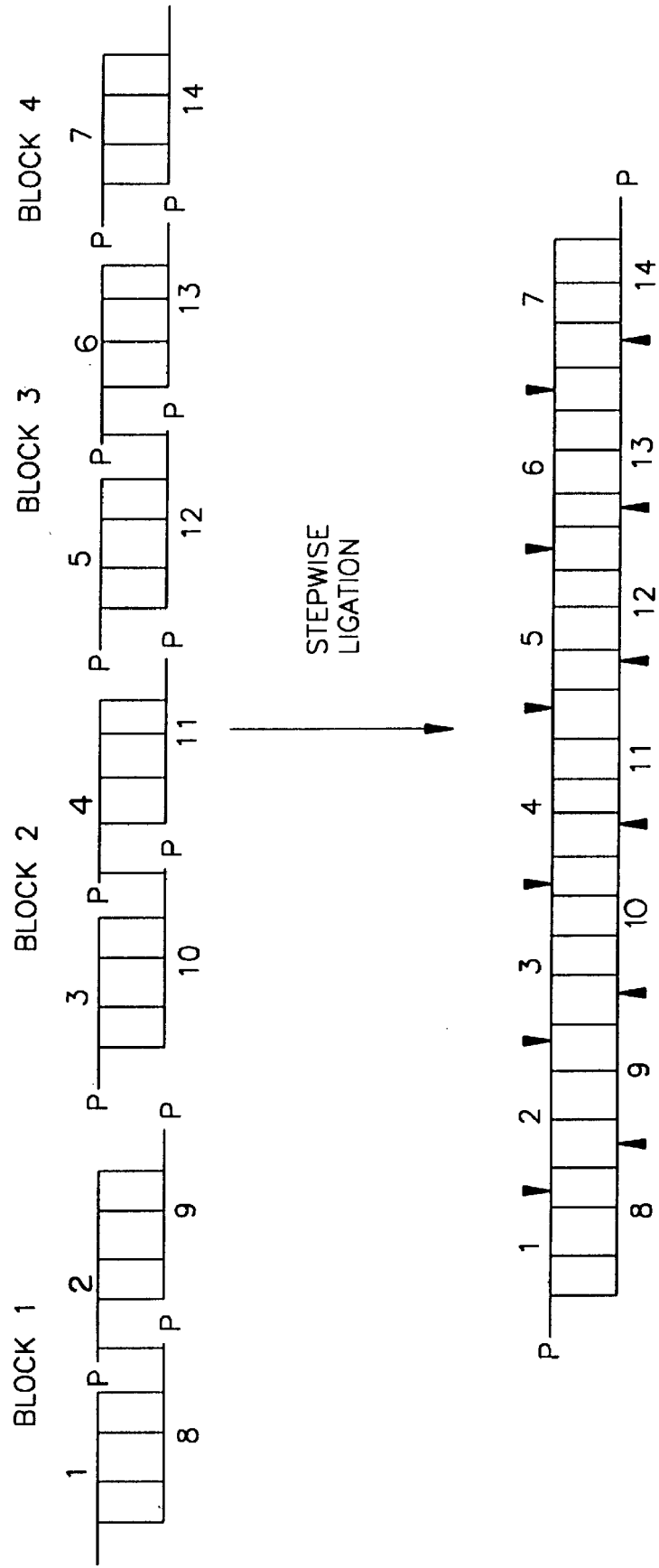
FIG. 2: Illustrates the assembly of the ENV93 synthetic gene which was constructed by stepwise ligation of 14 overlapping oligonucleotide fragments. The gene was divided into four blocks: Block 1: oligos 1, 2, 8, 9; Block 2: oligos 3, 4, 10, 11; Block 3: oligos 5, 6, 12, 13; Block 4: oligos 7, 14. All oligonucleotides except the 5' terminal fragments, 1 and 14, were phosphorylated at their 5' ends. Initially, the oligonucleotides comprising each block were annealed and ligated. The blocks were then annealed and ligated to each other to generate the ENV93 end product. Arrowheads mark the boundaries of the 14 oligonucleotide building blocks. The 5' termini of the duplex (oligos 1 and 14) were phosphorylated to facilitate insertion into the desired cloning vector.

The ENV93 synthetic gene was assembled via a stepwise ligation. The oligonucleotides were boiled for 2 minutes, spun down in the Eppendorf microcentrifuge, and allowed to cool at room temperature for 5 minutes. The 10 ul samples were then combined to form Blocks 1–4 as depicted in FIG. 2. The blocks were boiled 2 minutes, spun in microcentrifuge, and cooled at room temperature for 5 minutes. The blocks were incubated at 37° C. for 5 minutes and cooled at room temperature for 10 minutes. An equal volume of 2× ligation mix (50 mM Tris-HCl, pH 7.5; 10 mM $MgCl_2$, 20 mM DDT, 2 mM ATP) was added to each block containing the annealed oligonucleotides. 400–800 units of T4 DNA ligase (New England Biolabs) were added to each block ligation and the reactions (ligation reaction #1) were incubated at 14° C. for 16 hours. The ligase was inactivated by the addition of EDTA to 10 mM.

One-tenth of each ligation reaction was removed for analysis on a 10% polyacrylamide gel containing 7M urea. The ligation reactions were adjusted to contain 0.3M NaOAc, pH 5.2 and extracted with an equal volume of phenol/chloroform/isoamyl alcohol (25:24:1). Subsequent to ether extraction, $MgCl_2$ was added to 10 mM and the ligation products were precipitated with two volumes of 100% ethanol. The ethanol pellets were recovered by centrifugation, washed with 70% ethanol, dried under vacuum, and resuspended in 10 ul of 50 mM Tris-HCl, pH 7.5; 10 mM $MgCl_2$. The next step was to anneal the four blocks by way of the 12–14 base pair overlaps (FIG. 2). The blocks were incubated at 37° C. for 10 minutes and cooled at room temperature for 5 minutes. The blocks were combined in a single tube and incubated at 37° C. for 10 minutes. The tubes were cooled slowly to 14° C. over a 30 minute period. An equal volume of 2× ligation mix and 800 units of T4 DNA ligase (New England Biolabs) were added and the reaction was maintained at 14° C. for 16 hours (ligation reaction #2). EDTA was added to 10 mM to inactivate the ligase. The 283 bp BamHI fragment was purified by electrophoresis in a 4% NUSIEVE GTG agarose/TAE minigel containing 0.5 ug/ml ethidium bromide. The uppermost band was excised and the fragment was phenol and ether extracted after the agarose was melted at 65° C. The DNA was ethanol precipitated and the recovered pellet was washed with 70% ethanol and dried under vacuum.

EXAMPLE 3

Cloning of ENV93 in pUC18

In order to verify the sequence of the ENV93 construct, the fragment was initially cloned into the pUC18 sequencing vector (Yanisch-Perron et al., Gene 33: 103 (1985) at the unique BamHI site.

The ENV93 DNA pellet (250 ng) was resuspended in distilled $H_2O$ and kinased in a 20 ul reaction which contained 50 mM Tris-HCl, pH 7.5; 10 mM $MgCl_2$, 5 mM DTT, 0.1 mM spermidine, 20 uM ATP, and 9 U T4 polynucleotide kinase. The kinase reaction was incubated at 37° C. for 40 minutes. The kinase enzyme was heat inactivated at 70° for 15 minutes. The reaction containing the ENV93 DNA was diluted 1:5 with distilled $H_2O$. Five ng of ENV93 DNA was ligated to 50 ng of dephosphorylated vector (1:1 molar ratio) at 14° C. for 16 hours. The reaction was adjusted to 10 mM EDTA and heated at 70° C. for 15 minutes. Competent *E. coli* RR1 cells (ATCC No. 31343) were transformed with the mixture and ampicillin-resistant colonies were obtained. Transformants which appeared to contain the ENV93 construct based upon BamHI digestion were subjected to dideoxy sequencing. M13 universal sequencing primers which hybridize to opposite strands of the vector just outside the polylinker cloning site were initially used in conjunction with the Promega dideoxy sequencing system to generate sequence information on both strands of the insert. Additional 17-mer primers specific for ENV93 were necessary to complete the sequence of both strands of the ENV93 duplex. The insert of a clone with the correct ENV93 construction was gel purified in preparation for ligation into the expression vector.

EXAMPLE 4

Cloning of ENV93 in pDS56/RBSII

The ENV93 synthetic gene was directly ligated into the BamHI site of the appropriate reading frame pDS56/RBSII expression vector (Stueber et al., referenced previously) as outlined in FIG. 3. The vector was linearized with BamHI, dephosphorylated, and isolated away from the pDMI-1 compatible plasmid by electrophoresis in a 0.7% agarose/TAE minigel. The DNA was purified from the agarose using Geneclean (Bio 101). Five ng of insert were ligated to 60 ng of vector (1:1 molar ratio) in a 20 ul reaction maintained at 14° C. for 16 hours. Half the ligation mixture was used to transform competent *E. coli* W3110 cells (ATCC No. 27325). The DNAs of ampicillin/kanamycin resistant clones were screened by restriction enzyme digestion for the presence of ENV93 inserts ligated in the expression vector in the proper orientation for protein expression. A number of positive clones were identified and the DNA of one of them was used to transform *E. coli* strains: JE5505, JE5506. (Hirota, et al., P.N.A.S., 74: 1417 (1977)).

The insertion of the ENV93 epitope into the pDS56/RBSII vector results in the translation of a recombinant protein of 106 amino acids. The deduced amino acid sequence and coding nucleotides of the actual protein expressed from the ENV93 construct are shown in FIG. 4. The vector sequences contribute three amino acids at the N-terminus and 10 amino acids at the C-Terminus of the protein which are not specified by the HTLV-I genome.

EXAMPLE 5

Expression of the ENV93 Epitope in *E. coli*

Expression of the recombinant protein was achieved by isopropyl-β-D-thiogalactoside (IPTG) induction of an actively growing bacterial culture as described by Certa et al. *EMBO J.* 5: 3051 (1986) with modifications. *E. coli* cultures were grown to an $OD_{600}$ of 0.6–0.7 at 37° C. (time 0). At this time point a 1 ml aliquot was removed. The culture was split into two flasks and into one flask, IPTG was added to 0.5 mM. The cultures were incubated at 37° C. and 1 ml aliquots were taken at 2 and 4 hours post-induction. The bacterial cells were collected by centrifugation and resuspended in lysis buffer (125 mM Tris-HCl, pH 6.8; 10% glycerol, 2% SDS, 0.1% BPB, 1.25% 2-mercaptoethanol). Equivalent amounts of whole cell lysate were electrophoresed in a 12% polyacrylamide/SDS gel using the discontinuous buffer system described by Laemmli *Nature* 277: 80 (1970). Samples were denatured by boiling prior to loading on the gel. Proteins were visualized by staining with Coomassie Brilliant Blue R250.

Figure 5:
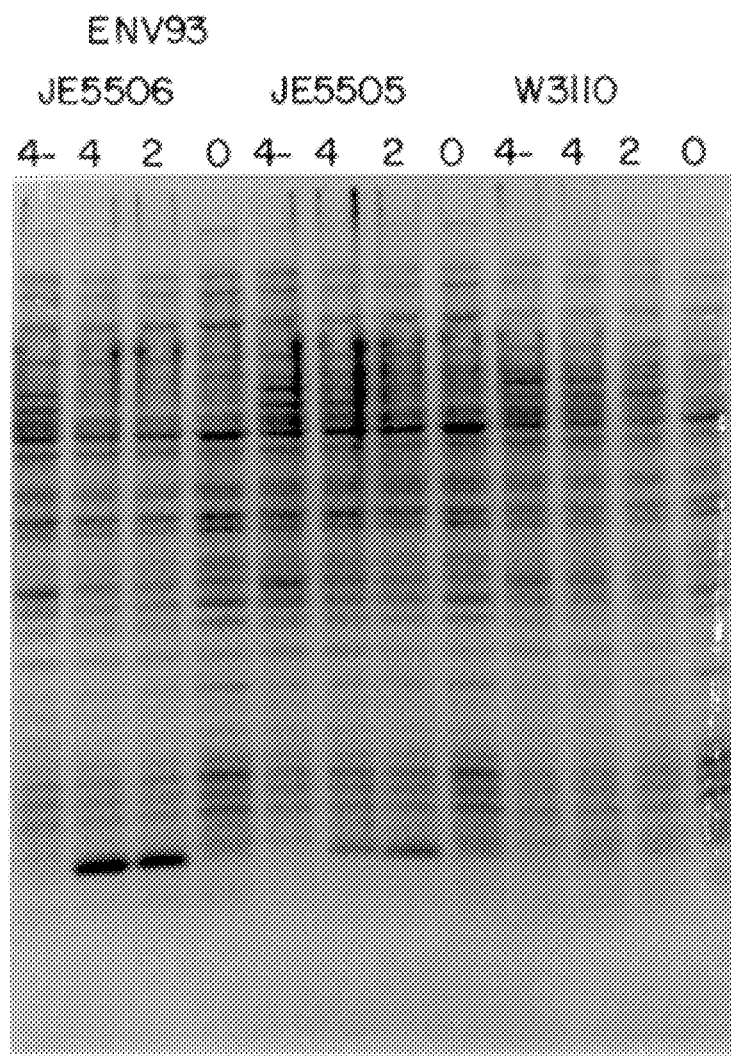
FIG. 5: Illustrates the expression of the HTLV-I ENV93 protein in *E. coli* cells W3110, JE5505, and JE5506. Whole cell lysates derived from bacterial cultures at time 0, 2 hours post-induction, 4 hours post-induction, and 4 hours no induction were electrophoresed in a 12% polyacrylamide/SDS cell stained with Coomassie Blue R250. The arrowhead indicates the position of the ENV93 protein of approximately 12 Kd which is only present in the IPTG-induced samples.

FIG. 5 shows expression of the ENV93 recombinant protein in three *E. coli* host strains harboring the pDS56/RBSII ENV93 construct. The ENV93 polypeptide of 12 Kd is expressed at different levels in the *E. coli* strains tested. The JE5506 host produces the highest levels of ENV93 in the W3110 host:, ENV93 is barely detected by Coomassie staining.

EXAMPLE 6

Purification of Recombinant ENV93 Protein

The recombinant protein was purified according to Manne et al. *P.N.A.S. USA* 82: 376 (1985) with modifications. An induced cell pellet form a 500 ml bacterial culture was resuspended in 25 ml of Buffer 1 (10 mM Tris-HCl, pH 8; 2 mM EDTA, 1 mM DTT). The solution was centrifuged at 12,000×g for 10 minutes at: 4° C. The pellet was resuspended in 10 ml of Buffer 1. Lysozyme was added to 0.75 mg/ml and the suspension was incubated at 37° C. for 15 minutes. $MgCl_2$ was added to 23 mM and 4.5 mg of DNase I. The suspension was maintained at 37° C. for 30 minutes. Twenty-five ml of Buffer 2 (10 mM Tris-HCl, pH 8; 1 mM DTT) was added and the lysate was centrifuged at 12,000×g for 10 minutes at 4° C. The pellet was washed with 25 ml of Buffer 2 and centrifuged at 12,000×g for 10 minutes at 4° C. The pellet was brought up in 25 ml of Buffer 3 (10 mM Tris-HCl, pH 8; 1 mM DTT, 0.15M NaCl, 0.5% Triton X-100). The solution was kept for 15 minutes at 0° C., 30 minutes at 37° C., and 15 minutes at 0° C. The sample was centrifuged at 12,000×g for 10 minutes at 4° C. The pellet was washed with 25 ml of Buffer 2 and collected by centrifugation. The pellet was resuspended in 0.2 ml of Buffer 2 and solubilized by the addition of 3.8 ml of Buffer 4 (10 mM Tris-HCl, pH 8; 7M GuHCl, 5 mM DTT). Insoluble material was removed by centrifugation. The supernatant was diluted 1:15 with Buffer 6 (10 mM Tris-HCl, pH 8; 5 mM DTT) and incubated for 10 minutes at room temperature to precepitate the protein. The protein was collected by centrifugation at 12,000×g for 10 minutes at 4° C. The pellet was washed with 20 ml of Buffer 6 and collected by centrifugation. The resulting pellet was slowly dissolved in 3 ml of Buffer 5 (125 mM Tris-HCl, pH 6.8; 4% (w/v) SDS, 5 mM DTT, 0.02% $NaN_3$). Further purification was achieved by chromatography on a Sephacryl S-200 (Pharmacia) 1.6×95 cm column equilibrated in 25 mM Tris-HCl, pH 8; 5 mM DTT, 0.1% SDS, 1 mM EDTA, 0.1M NaCl, and 0.02% $NaN_3$. Fractions were analyzed by SDS-PAGE. The fractions containing the protein of interest were pooled and the protein concentration was determined by UV absorbance at 280 nm. The pooled material was used for coating polystyrene beads in the enzyme immunoassay.

EXAMPLE 7

Expression of Envelope Epitopes as ENV93 Fusion Proteins

The ENV93 construct is being utilized as a convenient vehicle for efficient expression of other regions of the HTLV-I genome. This system should make available sufficient quantities of HTLV-I recombinant proteins necessary for evaluation as test antigens in an antibody screening assay.

Figure 6:
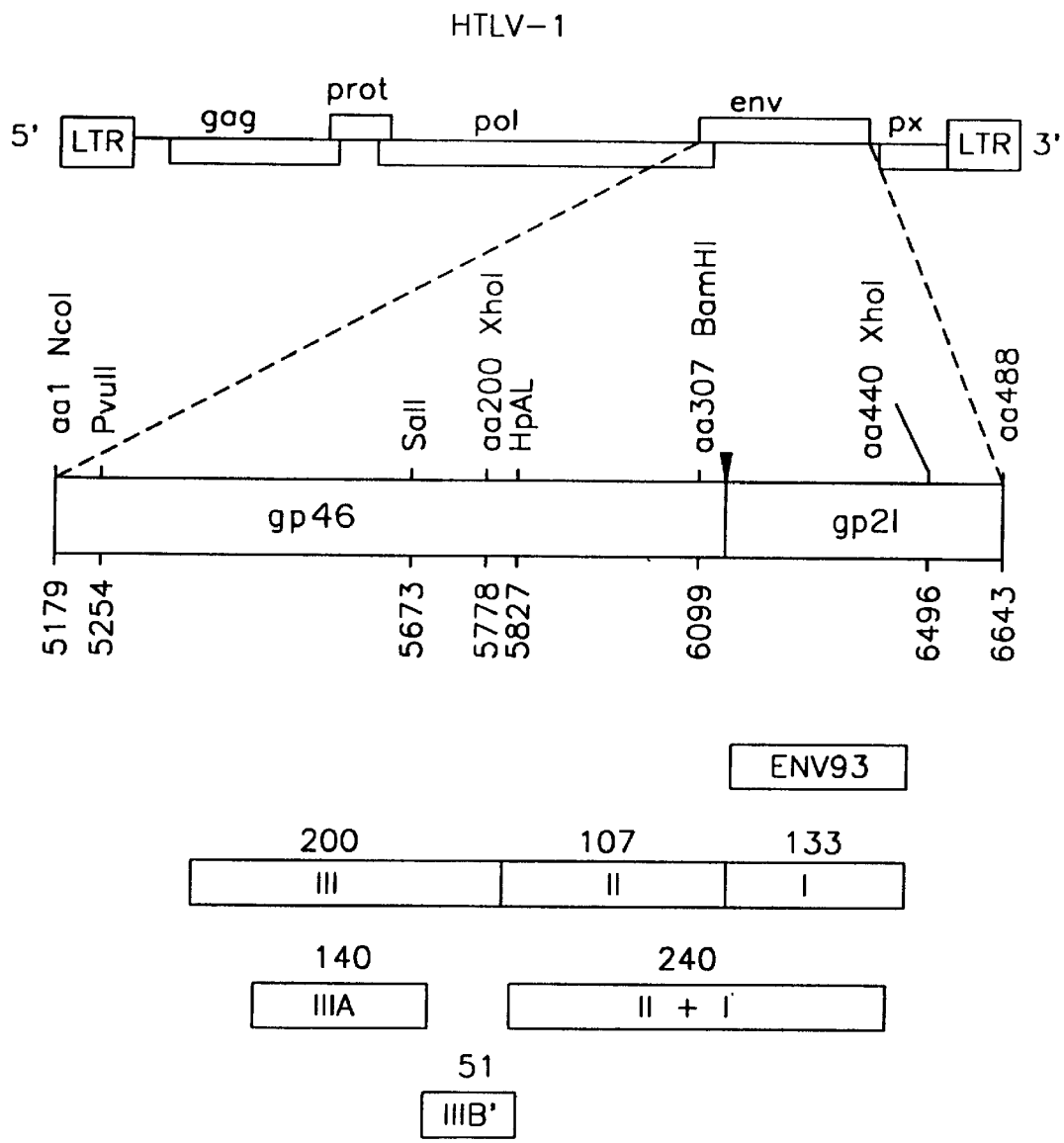
FIG. 6: Illustrates the structure of the HTLV-I proviral genome shown schematically. The complete nucleotide sequence of the genome was determined by Seiki et al. *P.N.A.S., USA* 80: 3618 (1983). The envelope coding region is enlarged to show nucleotide and amino acid positions of restriction sites within the gp46 and gp21 domains. The map position of the ENV93 synthetic gene construct is indicated. The restriction sites shown were used to generate the envelope fragments III, IIIA, IIIB', II, I, and II+I which encompass nearly the entire coding region. The number of amino acids represented in each fragment is indicated directly above the fragment. These DNA pieces were cloned downstream of ENV93 in the pDS56/RBSII vector to obtain high level expression of the encoded epitopes as ENV93 fusion proteins.
Figure 7:
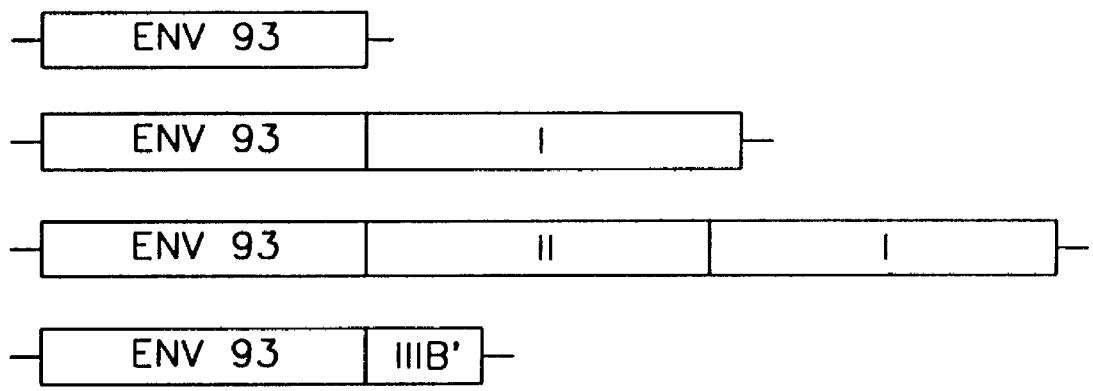
FIG. 7: Illustrates HTLV-I envelope expressed proteins. Various regions of the envelope coding sequence were ligated downstream of the ENV93 synthetic gene in the pDS56/RBSII vector. Recombinant fusion proteins were expressed in *E. coli* and those proteins possessing the greatest reactivity in the EIA are illustrated.

The source of HTLV-I envelope DNA is plasmid pH2Ex. This plasmid was originally subcloned from lambda CR1 which contains env, pX, and the 3' LTR of HTLV-I (Manzari et al., *P.N.A.S. USA* 80: 1574 (1983); European Patent Application Publication No. 0 181 107). A map of the envelope coding region is shown in FIG. 6. The restriction sites indicated were used to generate the following DNA fragments: III, IIIA, IIIB', II, I, and II+I. These DNA represent nearly the entire envelope coding sequence. Each fragment was inserted downstream of ENV93 in pDS56/RBSII and recombinant fusion proteins as depicted in FIG. 7 were expressed in *E. coli* and purified as described previously.

EXAMPLE 8

Construction of ENV93/HTLVI-IIIB'

A 154 bp SalI/HpaI fragment (nts 5672–5827) was isolated from pH2Ex (FIG. 6). This IIIB' DNA encodes 52 amino acids corresponding to amino acids 166–216 of the gp46 envelope domain. SalI synthetic 8-mer linkers were added to the fragment and the IIIB' was ligated into the SalI site of ENV93/pDS56/RBSII. The nucleotide and deduced amino acid sequence of the fusion protein expressed from the construct: are presented in FIG. 8. The 158 amino acid protein of 17.8 Kd shows the highest level of expression in the JE5506 cell strain (data not shown).

Construction of ENV93/HTLVI-I

The 718 bp XhoI fragment (nts 5780–6499, FIG. 6) was subcloned into the SalI site of pDS56/RBSII to generate the pBSEVN construct. This DNA was digested with BamHI/HindIII to release the 413 bp I fragment. The I fragment encodes 133 amino acids corresponding to amino acids 308–440 of the envelope polypeptide. The C-terminus of gp46 along with most: of the gp21 domain is included in fragment I. The addition of 10-mer HindIII linkers was necessary to insert the I fragment into the HindIII site of ENV93/pDS56/RBSII. The nucleotide and deduced amino acid sequence of the expressed fusion protein are shown in FIG. 9. The polypeptide of 245 amino acids has a molecular weight of 27 Kd. The ENV93/HTLVI-I construct directs the expression of a double dose of ENV93 epitopes. The entire ENV93 sequence is included within the I fragment.

Construction of ENV93/HTLVI-II+I

The 718 bp XhoI fragment (nts 5780–6499) was isolated from pH2Ex and ligated directly into the compatible SalI site of ENV93/pDS56/RBSII. The II+I fragment codes for 240 amino acids corresponding to residues 201–440 of the HTLV-I envelope polypeptide. Epitopes derived from gp46 and gp21 are represented in the II+I fragment. The recombinant fusion protein expressed from this construct is 344 amino acids which translates into a molecular weight of 37.9 Kd. The nucleotide and deduced amino acid sequence of the ENV93/HTLVI-II+I protein are shown in FIG. 10.

Construction of ENV93/HTLVI-II

The pbsENV DNA was digested with BamHI to release the 328 bp II fragment. The II fragment encodes amino acids 201–308 at the C-terminus of the gp46 envelope protein (FIG. 6). The 5' BamHI sticky ends were filled in with Klenow enzyme and 10-mer HindIII linkers were ligated to the DNA to facilitate insertion into the HindIII site of ENV93/pDS56/RBSII. The nucleotide and deduced amino acid sequence of the expressed fusion protein are shown in FIG. 11. The ENV93/HTLVI-II protein of 217 amino acids has a molecular weight of 24 Kd.

Construction of ENV93/HTLVI-III

The III fragment represents the N-terminus of gp46 from amino acids 1–200. The III fragment was isolated from pH2Ex by NcoI/XhoI digestion (FIG. 6) and the 599 bp DNA was subcloned in the HindIII site of pENV59 via the ligation of synthetic HindIII linkers. The III fragment was purified from the pENV59/HTLVI-III DNA construct as a 613 bp HindIII fragment. The 5' HindIII sticky ends were filled in with Klenow enzyme and 10-mer HindIII linkers were ligated to the blunt-ended DNA. The insert was ligated into the HindIII site of ENV93/pDS56/RBSII. The nucleotide and deduced amino acid sequence of the expressed recombinant protein are presented in FIG. 12. The ENV93/HTLVI-III polypeptide has a molecular weight of 35 Kd and consists of 315 amino acids.

Construction of ENV93/HTLVI-IIIA

The IIIA fragment was derived from ENV59/HTLVI-III by PvuII/AslI digestion (FIG. 6). The IIIA fragment encodes amino acids 26–166 of the gp46 protein. The 5' SalI end of the 419 bp fragment was filled in with Klenow enzyme and 10-mer SalI linkers were ligated for insertion at the unique SalI site of ENV93/pDS56/RBSII. The nucleotide and deduced amino acid sequence of the expressed ENV93/HTLVI-IIIA fusion protein are shown in FIG. 13. The 28 Kd polypeptide is 249 amino acids in length.

EXAMPLE 9

Enzyme Immunoassay (EIA)

Purified HTLV-I recombinant proteins were coated on polystyrene beads (¼ in. diameter) at a final concentration of 10 ug/ml in 0.05M carbonate-bicarbonate buffer, pH 9.5. Coating was for 18 hours at 37° C. Unbound proteins were removed by washing with deionized water and the beads were dried at 37° C. and stored desiccated at 4° C. HTLV-I positive and negative sera were prediluted by dispensing 10 ul of sera with 400 ul of sample diluent (20% newborn calf serum, 0.5% Tween 20, 0.01% goat IgG, 0.01% Thimerosal, 5 mM EDTA in 0.002M phosphate buffered saline, pH 7.0) into the reaction tube. One coated bead was added to the tube and incubated in a COBAS RESA shaker/incubator for 30 minutes at 37° C. Unbound antibodies were removed by washing with deionized water in a COBAS RESA automatic bead washer. 250 ul of goat anti-human IgG labeled with horseradish peroxidase (Boehringer Mannheim) was diluted 1:9000 in conjugate diluent (0.1M Tris-acetate, pH 7.3 containing 20% fetal calf serum, 0.04% 4-amino antipyrine, 1% Tween 20, 0.1% (v/v) Kathon) and added to the reaction tube. Incubation was in the COBAS RESA shaker/incubator for 15 minutes at 37° C. Free conjugates were removed by washing with deionized water. 250 ul of substrate solution (2 mg/ml o-phonylenediamine in 0.1M potassium citrate, pH 5.25; 0.02% hydrogen peroxide, 0.01% Kathon) was added to each tube and incubated for 15 minutes at room temperature. The reaction was terminated by addition of 1 ml of 1N sulfuric acid. Optical density at 492 nm was measured in a COBAS RESA spectrophotometer. EIA results for the HTLV-I recombinant fusion proteins are presented in FIG. 14. The ENV93/HTLVI-II+I protein shows the greatest reactivity with the tested positive serum samples.

We claim:

1. A hybrid polypeptide comprising a first amino acid sequence fused at its carboxy terminus to a second amino acid sequence, wherein the first sequence consists of amino acids 342–434 of HTLV-I env which has the formula:

Ser Gly Lys Ser Leu Leu His Glu Val Asp Lys Asp Ile Ser Gln Leu Thr
342 345 350 355
Gln Ala Ile Val Lys Asn His Lys Asn Leu Leu Lys Ile Ala Gln Tyr Ala
360 365 370 375
Ala Gln Asn Arg Arg Gly Leu Asp Leu Leu Phe Trp Glu Gln Gly Gly Leu
380 385 390
Cys Lys Ala Leu Gln Glu Gln Cys Arg Phe Pro Asn Ile Thr Asn Ser His
395 400 405
Val Pro Ile Leu Gln Glu Arg Pro Pro Leu Glu Asn Arg Val Leu Thr Gly
410 415 420 425
Trp Gly Leu Asn Trp Asp Leu Gly
430 434 and the second amino acid sequence contains at least one epitope selected from the group consisting of epitopes from HTLV-I env gp46, gp21, or both HTLV-I env gp46 and gp21, and wherein when the second amino acid sequence is from gp21 alone, the second sequence contains said amino acids 342–434 of HTLV-I env.

2. The polypeptide of claim 1 wherein the second amino acid sequence is amino acids 308–440 of HTLV-Ienv (I).

3. The polypeptide of claim 1 wherein the second amino acid sequence is amino acids 201–308 of HTLV-Ienv (II).

4. The polypeptide of claim 1 wherein the second amino acid sequence is amino acids 201–440 of HTLV-Ienv (II+I).

5. The polypeptide of claim 1 wherein the second amino acid sequence is amino acids 1–200 of HTLV-Ienv (III).

6. The polypeptide of claim 1 wherein the second amino acid sequence is amino acids 26–166 of HTLV-Ienv (IIIA).

7. The polypeptide of claim 1 wherein the second amino acid sequence is amino acids 165–216 of HTLV-Ienv (IIIB').

* * * * *